(12) United States Patent
Hasenberg et al.

(10) Patent No.: US 7,645,906 B2
(45) Date of Patent: *Jan. 12, 2010

(54) GRADED CATALYST BED FOR METHYL MERCAPTAN SYNTHESIS

(75) Inventors: Daniel M Hasenberg, Humble, TX (US); Mitchell D Refvik, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/691,615

(22) Filed: Mar. 27, 2007

(65) Prior Publication Data

US 2008/0242894 A1    Oct. 2, 2008

(51) Int. Cl.
C07C 319/00 (2006.01)

(52) U.S. Cl. .......................... 568/61; 502/300

(58) Field of Classification Search ............... 502/255, 502/260, 238, 247, 256, 261, 241, 242; 568/38, 568/59, 71
See application file for complete search history.

(56) References Cited

U.S. PATENT DOCUMENTS

| | | | |
|---|---|---|---|
| 3,035,097 A | 5/1962 | Deger | |
| 3,963,785 A | 6/1976 | Kubicek | |
| 3,994,980 A | 11/1976 | Kubicek | |
| 4,055,514 A | 10/1977 | Elion et al. | |
| 4,342,699 A | 8/1982 | Palmer et al. | |
| 5,011,945 A | 4/1991 | Taheri | |
| 5,283,369 A | 2/1994 | Clark et al. | |
| 5,352,838 A | 10/1994 | Sattich | |
| 5,453,544 A | 9/1995 | Giacobbe | |
| 5,733,836 A * | 3/1998 | Stinn et al. | 502/255 |
| 5,874,630 A | 2/1999 | Cook et al. | |
| 5,898,012 A | 4/1999 | Stinn et al. | |
| 6,005,121 A | 12/1999 | Ebner et al. | |
| 6,198,003 B1 | 3/2001 | Lin et al. | |
| 7,368,611 B2 * | 5/2008 | Barth et al. | 568/71 |
| 2007/0135658 A1 * | 6/2007 | Hasenberg et al. | 568/38 |
| 2008/0015390 A1 * | 1/2008 | Redlingshoefer et al. | 568/61 |

FOREIGN PATENT DOCUMENTS

| | | |
|---|---|---|
| EP | 0354460 | 2/1990 |
| EP | 0564706 | 10/1993 |

(Continued)

OTHER PUBLICATIONS

Paskach et al., Synthesis of Methanethiol from Methanol over Reduced Molybdenum Sulfide Catalysts Based on the Mo6S8 Cluster Journal of Catalysis (2002), 211(2), 285-295.*

(Continued)

*Primary Examiner*—Sikarl A Witherspoon
*Assistant Examiner*—Chukwuma O Nwaonicha

(57) ABSTRACT

A process and graded catalyst bed for selectively producing methyl mercaptan from methanol. The methanol is reacted with hydrogen sulfide, in the presence of a graded catalyst bed containing at least three types of nickel or cobalt molybdenum alumina catalysts to convert the methanol to methyl mercaptan in one-pass. At least one of the hydrotreating catalysts can contain aluminium phosphate. Use of the graded catalyst bed prevents the formation of a hot spot within the graded catalyst bed. The methyl mercaptan having less than about 30 wt. % unreacted methanol contained therein.

15 Claims, 1 Drawing Sheet

FOREIGN PATENT DOCUMENTS

| | | |
|---|---|---|
| EP | 0651041 A1 | 5/1995 |
| EP | 0796656 | 9/1997 |
| EP | 0593646 | 12/1998 |
| EP | 1005906 | 6/2000 |
| EP | 0929503 | 10/2001 |
| WO | WO/ 01/51411 | 7/2001 |
| WO | WO 2007/070496 A2 | 6/2007 |

OTHER PUBLICATIONS

Mashkina et al. Synthesis of methyl mercaptan from methanol and hydrogen sulfide in the presence of acid catalysts, Kinetika i Kataliz (1988), 29(3), 596-602 (Abstract).*

Ziolek et al., Effect on the reaction between methanol and hydrogen sulfide of Na or Mo doping on zirconia and alumina, Applied Catalysis, A: General (1998), 171(1), 109-115.*

Haldor Topsoe, Inc. Product Sheet for Hydroprocessing Catalyst TK-711.

Haldor Topsoe, Inc. Product Sheet for Hydroprocessing Catalyst TK-573.

Haldor Topsoe, Inc. Product Sheet for Hydroprocessing Catalyst TK-751.

Anonymous, Topsoe Refinery Catalysts: Pressure Drop Control, Mar. 22, 2006, pp. 1-8.

Partial International Search Report, PCT/US08/058174, Aug. 8, 2008, 5 pages.

International Search Report and Written Opinion, PCT/US08/058174, Oct. 9, 2008, 17 pages.

F.E.Massoth, Kinetics of the HDN of Quinoline under Vapor-Phase Conditions, Ind. Eng. Chem. Res. 2003, 42, 1011-1022.

* cited by examiner

GRADED CATALYST BED FOR METHYL MERCAPTAN SYNTHESIS

TECHNICAL FIELD OF THE INVENTION

The present invention relates to a process for selective production of methyl mercaptan. More specifically, the present invention relates to a process for producing methyl mercaptan utilizing a combination of catalysts.

BACKGROUND OF THE INVENTION

Mercaptans, which are also known as thiols, are organic compounds that are used in diverse applications. Some mercaptans, such as methyl mercaptan ($CH_3SH$), are used as natural gas odorants, agricultural supplements, or as polymerization process modifiers. Methyl mercaptan is used in organic synthesis of sulfur compounds and as an intermediate for jet fuel additives and fungicides. Methionine, which is an essential amino acid, is one type of synthetic sulfur compound that can be produced from mercaptans.

Many types of synthetic sulfur compounds exist. The variety of synthetic sulfur compounds available can be attributed to the numerous mercaptan compounds that can be synthesized. Yet, while numerous compounds can be made, economical processes for the production of even relatively simple mercaptans, such as methyl mercaptan, are not available in some cases.

Mercaptans can be produced from alcohols using various catalysts. Unfortunately, thermodynamic conditions in most alcohol reactions using traditional catalysts result in poor efficiencies because of the lack of uniform temperature distribution throughout the catalyst bed. A need exists for an economic and efficient process for selective production of simple mercaptans, such as methyl mercaptan from alcohols.

SUMMARY OF THE INVENTION

In view of the foregoing, a process for selective production of methyl mercaptan using a graded catalyst bed is provided as an embodiment of the present invention. Methanol and hydrogen sulfide are contacted with the graded catalyst bed. The methanol and the hydrogen sulfide react to produce the methyl mercaptan. During the process, near isothermal conditions are maintained. The graded catalyst bed generally contains three catalysts with each catalyst having a lower activity for convert methanol to the methyl mercaptan than the subsequent catalyst The catalysts within the graded catalyst bed generally have an activity for converting the methanol to the methyl mercaptan that increases from an inlet to an outlet of the graded catalyst bed. The activity for converting the methanol to the methyl mercaptan increases from the first catalyst to the second catalyst to the third catalyst. Catalysts useful in the present invention are generally referred to as hydrotreating catalysts.

A first catalyst has a lower activity for converting methanol to methyl mercaptan than a second catalyst. The second catalyst has a lower activity for converting methanol to methyl mercaptan than a third catalyst. In an aspect, the first, second, and third catalysts include an oxide of molybdenum and an oxide of cobalt supported on alumina. In another aspect, the first, second, and third catalysts include an oxide of molybdenum and an oxide of nickel supported on alumina. In an aspect, the first, second, and third catalysts can include an oxide of molybdenum and an oxide of cobalt supported on alumina, an oxide of molybdenum and an oxide of nickel supported on alumina, or a combination thereof.

The first, second, and third catalysts can comprise about 0.5 wt. % to about 5 wt. % nickel monoxide, about 3 wt. % to about 30 wt. % molybdenum trioxide, and about 50 wt. % to about 95 wt. % alumina. The second and third catalysts can further comprise about 2 wt. % to about 10 wt. % aluminium phosphate. In some embodiments, the first, second, and third catalysts can include a cobalt monoxide.

BRIEF DESCRIPTION OF THE DRAWINGS

So that the features, advantages, and objects of the invention can be understood in more detail, a more particular description of the invention briefly summarized above can be had by reference to the embodiments illustrated in the appended drawings, which form a part of this specification. The drawings illustrate only particular embodiments of the invention and are therefore not to be considered limiting of the invention's scope as it can admit to other equally effective embodiments.

DETAILED DESCRIPTION OF THE INVENTION

Figure 1:
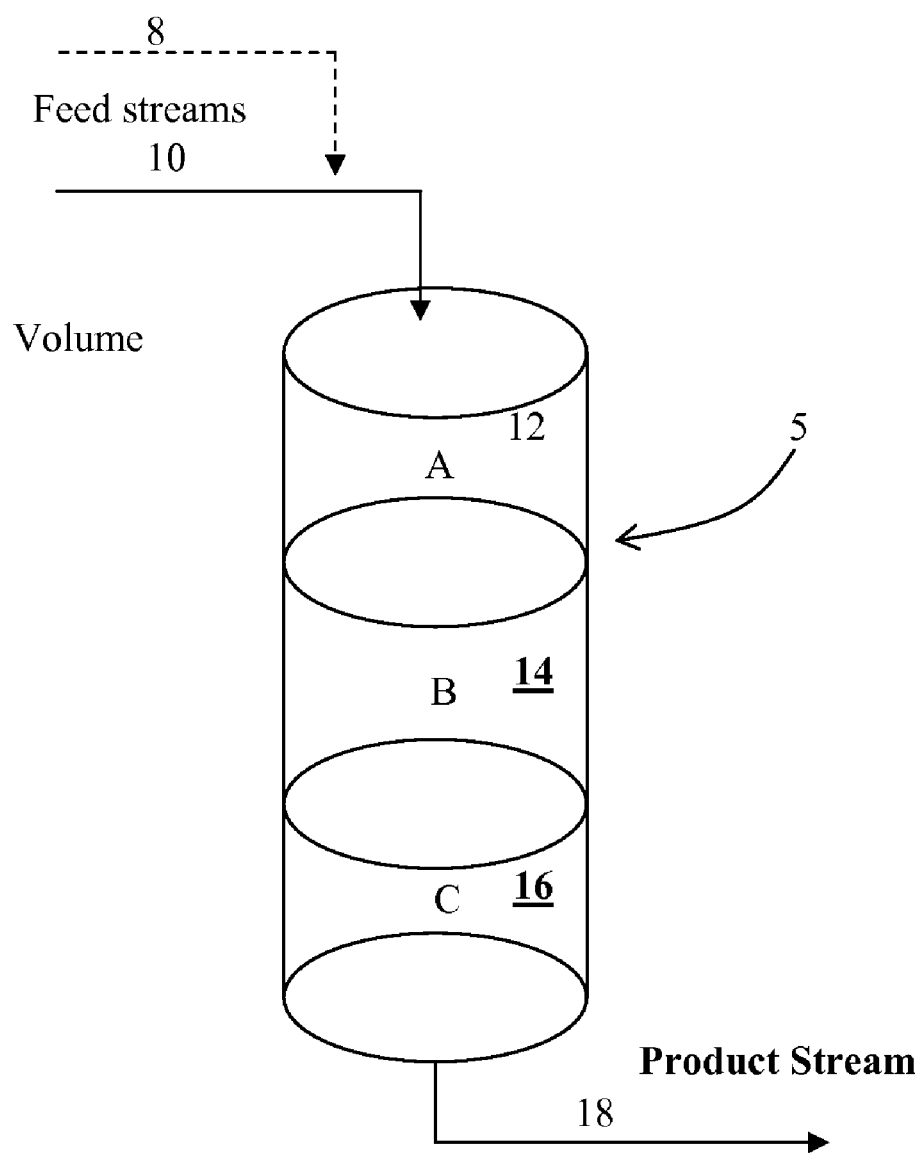
FIG. 1 is a perspective view of a chemical reactor having a graded catalyst bed in accordance with an embodiment of the present invention.

A process for selcetive production of methyl mercaptan is provided as an embodiment of the present invention. As shown in FIG. 1, methanol 8 and hydrogen sulfide 10 are contacted with a graded catalyst bed 5 that comprises at least three catalysts A, B, C. The three catalysts A, B, C can generally be referred to as hydrotreating catalysts. The three catalysts A, B, C generally have an activity for converting methanol 8 to methyl mercaptan 18 that increases from the first catalyst A to the second catalyst B to the third catalyst C. The first catalyst A has a lower activity for converting methanol 8 to methyl mercaptan 18 than the second catalyst B. The second catalyst B has a lower activity for converting methanol 8 to methyl mercaptan 18 than the third catalyst C. Generally, each subsequent catalyst has a higher activity for converting methanol 8 to methyl mercaptan 18 than the catalyst prior to it The methanol 8 and the hydrogen sulfide 10 are reacted to produce the methyl mercaptan 18 while maintaining near isothermal conditions during reaction of the methanol 8 and the hydrogen sulfide 10. In some aspects, the methyl mercaptan 18 is produced in one process pass.

The first, second, and third catalysts A, B, C comprise either an oxide of molybdenum and an oxide of cobalt supported on alumina or an oxide of molybdenum and an oxide of nickel supported on alumina. The type, kind, amount, and properties of the first, second, and third catalysts A, B, C are independent elements that can be varied. For example, first catalyst A and third catalyst C can comprise an oxide of molybdenum and an oxide of cobalt supported on alumina, while second catalyst B can comprise an oxide of molybdenum and an oxide of nickel supported on alumina.

The primary reaction during synthesis of methyl mercaptan 18 from methanol 8 is as follows:

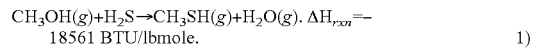

The reactions to make co-product dimethyl sulfide (DMS) are as follows:

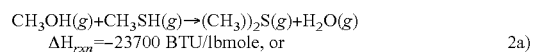

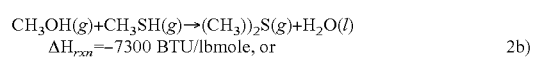

$2CH_3OH(g)+H_2S \rightarrow (CH_3)_2S(g)(DMS)+H_2O(g)$
$\Delta H_{rxn}=-42300$ BTU/lbmole, or (3a)

$2CH_3OH(l)+H_2S \rightarrow (CH_3)_2S(g)(DMS)+H_2O(l)$
$\Delta H_{rxn}=-47400$ BTU/lbmole. (3b)

Unwanted decomposition reactions are as follows:

$2CH_3OH(g) \rightarrow CH_4+H_2+CO_2$, and $\Delta H_{rxn}=-14200$ BTU/lbmole $CH_3OH$, and (4a)

$2CH_3OH(l) \rightarrow CH_4+H_2+CO_2$, and $\Delta H_{rxn}=3140$ BTU/lbmole $CH_3OH$, and (4b)

$2CH_3SH(g) \rightarrow CH_4+H_2+CS_2(g)$. $\Delta H_{rxn}=19000$ BTU/lbmole. (5)

Additionally, the activation energies for these reactions decrease in the order: 4>3>>2>1. Thus, lower temperatures enhance selectivity and feedstock efficiency of methanol to methyl mercaptan.

Upon examination of the $\Delta H_{rxn}$, it is apparent that the formation of methyl mercaptan from methanol and hydrogen sulfide and the formation of the by-product dimethyl sulfide are exothermic reactions that generate heat. The heat generated by the heat of reaction, unless dissipated and/or controlled, can produce reactor hot spots that will promote the reactions that form the dimethyl sulfide by-product and/or promote the decomposition reactions. Consequently, the present invention of using a graded reaction bed can be used to control the heat generated by the production of methyl mercaptan and reduce the production of the dimethyl sulfide by-product and the occurrence of the decomposition reactions.

Another aspect that can be used to reduce the formation of unwanted co-products includes feeding the methanol 8 and the hydrogen sulfide 10 at a preselected hydrogen sulfide to methanol molar feed ratio that ranges from about 6:1 to about 20:1. In some embodiments, the preselected hydrogen sulfide to methanol molar feed ratio that ranges from about 9:1 to about 15:1; or alternatively, from about 9:1 to about 12:1. Controlling the hydrogen sulfide to methanol molar feed ratio helps control and limit the amount of co-products, such as dimethyl sulfide, that are produced. In some embodiments, the reactor effluent comprising methyl mercaptan 18 contains less than about 20 wt. % dimethyl sulfide; alternatively, less than about 15 wt. %; or alternatively, less than about 10 wt. %. Hydrogen sulfide to methanol ratios exceeding those disclosed herein can be utilized, however, the expense of so may exceed any benefit that could be achieved.

In an aspect, the reactor effluent comprising the methyl mercaptan 18 contains less than about 40 wt. % unreacted methanol 8; alternatively, less than about 30 wt. % unreacted methanol; or alternatively, less than about 20 wt. % unreacted methanol. In an aspect, the Besides the molar feed ratio of the feedstock chemicals, other process operating conditions can be varied in embodiments of the present invention to help reduce the formation of unwanted co-products. For example, the graded catalyst bed 5 can be operated at a preselected temperature that can be varied in a range of about 220° C. to about 250° C.; or alternatively, from about 230° C. to about 240° C. As another example, the graded catalyst blend 5 can be operated at a preselected pressure that can be varied in a range of about 400 psig to about 600 psig; alternatively, from about 450 psig to about 550 psig; or alternatively, from about 450 psig to about 500 psig. Other process operating conditions can be varied to help reduce the formation of unwanted co-products as will be apparent to those of skill in the art and are to be considered within the scope of the present invention.

Besides process operating conditions, the physical configuration of the graded catalyst bed can be varied. For example, in an embodiment, the graded catalyst bed 5 comprises about 20% to about 35% of the first catalyst A, about 20% to about 35% of the second catalyst B, and about 35% to about 55% of the third catalyst C. As shown in FIG. 1, the first catalyst A is located upstream of the second catalyst B and the second catalyst B is located upstream of the third catalyst C.

Catalysts suitable for use in this invention as the catalysts A, B, C include at least one Group IIIA-VIIIA transition metal and a support. Some suitable catalysts for use as the catalysts A, B, C are known as sulfactive hydrogenation catalysts or hydrodesulfurization (HDS) catalysts. The catalysts A, B, C can include the oxides of Group VIA and Group VIIIA metals such as, but not limited to, cobalt, nickel, molybdenum, iron, tungsten, chromium, and platinum. Alternatively, the catalysts A, B, C can include the sulfides of Group VIA and Group VIIIA metals such as, but not limited to, cobalt, nickel, molybdenum, iron, tungsten, chromium, and platinum. In yet other embodiments, the catalysts A, B, C can include the oxides, sulfides, or mixtures thereof, of Group VIA and Group VIIIA metals such as, but not limited to, cobalt, nickel, molybdenum, iron, tungsten, chromium, and platinum. In some embodiments, the catalysts A, B, C comprise molybdenum. In some embodiments, the catalysts A, B, C include two transition metals. In particular embodiments, the catalysts A, B, C include cobalt and molybdenum. In other embodiments, the catalysts A, B, C include nickel and molybdenum. Some suitable catalysts are available from catalyst manufacturers such as Criterion, Engelhard, Haldor-Topsoe, Akzo, and Chevron.

In an aspect, the first, second, and third catalysts A, B, C each have a stoichiometric sulfur uptake in a range of about 3 wt. % to about 13 wt. %. In another aspect, the stoichiometric sulfur uptake increases from the first catalyst A to the second catalyst B to the third catalyst C. In some embodiments, the first catalyst A has a stoichiometric sulfur uptake in a range of about 3 wt. % to about 4 wt. %, the second catalyst B has a stoichiometric sulfur uptake in a range of about 4 wt % to about 5 wt. %, and the third catalyst C has a stoichiometric sulfur uptake in a range of about 11.5 wt. % to about 13 wt. %. The "stoichiometric sulfur uptake" is generally described as the amount of oxygen that is quantitatively replaced by sulfur upon exposure of the catalyst to sulfur. Water is a by-product when the oxygen in the catalyst is replaced by sulfur. In an aspect, the stoichiometric sulfur uptake of the first catalyst A is less than about 4 wt. %, the stoichiometric sulfur uptake of the second catalyst B is less than about 5 wt. % and higher than the stoichiometric sulfur uptake of the first catalyst A, and the stoichiometric sulfur uptake of the third catalyst C is less than about 13 wt. % and greater than the stoichiometric sulfur uptake of the second catalyst B. In an aspect, generally, each subsequent catalyst has a stoichiometric sulfur uptake that is greater than that of the catalyst before it.

In an aspect, the first catalyst A has a bulk density greater than about 37 lbs/ft³, the second catalyst B has a bulk density greater than about 38 lbs/ft³, and the third catalyst C has a bulk density greater than about 51 lbs/ft³. In an aspect, generally, each subsequent catalyst has a bulk density that is greater than that of the catalyst before it.

Generally, the hydrotreating catalysts A, B, C comprise an oxide of molybdenum and a support. In some embodiments, the hydrotreating catalysts A, B, C comprise an oxide, sulfide, or mixed oxide/sulfide of molybdenum. In other embodiments, the hydrotreating catalysts A, B, C comprise an oxide of molybdenum supported on alumina. Typically, the oxide of molybdenum is $MoO_3$. However, other oxides, sulfides or mixed oxides/sulfides of molybdenum can be used. Additionally, other molybdenum compounds, including oxides, sulfides, or mixed oxides/sulfides of molybdenum, which can be converted to $MoO_3$ upon oxidation, can also be used. While the applicable quantities of the oxide of molybdenum present in the catalyst are stated as wt. % of $MoO_3$, one skilled in the art will recognize that the applicable compositions include other molybdenum materials and the quantities of molybdenum materials that, upon oxidation, will yield the disclosed quantities of $MoO_3$ described herein. Typically, the hydrotreating catalysts A, B, C comprise from 5 wt. % to 40 wt. % of an oxide of molybdenum; alternatively, from 8 wt. % to 35 wt. %; alternatively, from 8 wt. % to 15 wt. %; alternatively, from 10 wt. % to 20 wt. %; or alternatively, from 15 wt. % to 30 wt. %.

In some embodiments, the hydrotreating catalysts A, B, C comprise an oxide of cobalt, an oxide of molybdenum, and a support. In other embodiments, the hydrotreating catalysts A, B, C comprise an oxide of cobalt and an oxide of molybdenum supported on alumina. The oxide of molybdenum and the support have been described herein and are generally applicable to the catalyst compositions comprising an oxide of cobalt, an oxide of molybdenum, and a support. Some suitable commercially available catalysts are commonly referred to as cobalt molybdate on alumina. Typically, the oxide of cobalt is CoO. However, other cobalt compounds, including oxides, sulfides, or mixed oxides and sulfides of cobalt, which can be converted to CoO upon oxidation can also be used. While the applicable quantities of the oxide of cobalt present in the catalysts are stated as wt. % of CoO, one skilled in the art will recognize that the applicable compositions include other cobalt materials and the quantities of cobalt materials that, upon oxidation, will yield the disclosed quantities of CoO described herein.

In some embodiments, the hydrotreating catalysts A, B, C comprising an oxide of cobalt, an oxide of molybdenum, and a support can comprise from 1 to 10 wt. % of an oxide of cobalt. In other embodiments, the hydrotreating catalysts A, B, C comprising an oxide of cobalt, an oxide of molybdenum, and a support can comprise from 2 wt. % to 7 wt. % of an oxide of cobalt; or alternatively, from 3 wt. % to 5 wt. % of an oxide of cobalt. In some embodiments, the hydrotreating catalysts A, B, C comprising an oxide of cobalt, an oxide of molybdenum, and a support can comprise from 8 wt. % to 35 wt. % $MoO_3$, from 1 wt. % to 10 wt. % CoO, and from 50 wt. % to 91 wt. % alumina; alternatively, from 10 wt. % to 20 wt. % $MoO_3$, from about 3 wt. % to 5 wt. % CoO, and from 75 to 87 wt. % alumina; or alternatively, from 15 wt. % to 30 wt. % $MoO_3$, from 3 wt. % to 5 wt. % CoO, and from 65 wt. % to 82 wt. % alumina. In further embodiments, the hydrotreating catalysts A, B, C can also contain from 0.05 wt. % to 1 wt. % $Na_2O$. In other embodiments, the hydrotreating catalysts A, B, C can also contain up to 0.05 wt. % iron. In embodiments in which the hydrotreating catalysts A, B, C also contain iron, the iron can be present as elemental iron or as an oxide.

In some embodiments, the hydrotreating catalysts A, B, C comprise an oxide of nickel, an oxide of molybdenum, and a support. In other embodiments, the hydrotreating catalysts A, B, C comprise oxides of nickel and an oxide of molybdenum supported on alumina. The oxide of molybdenum and the support have been described herein and are generally applicable to the catalysts comprising an oxide of nickel, an oxide of molybdenum, and a support described herein. Typically, the oxide of nickel is NiO. However, other nickel compounds, including oxides, sulfides, or mixed oxides and sulfides of nickel, which can be converted to NiO upon oxidation can also be used. While the applicable quantities of the oxide of nickel present in the hydrotreating catalysts A, B, C are stated as wt. % of NiO, one skilled in the art will recognize that the applicable compositions include other nickel materials and the quantities of nickel materials that, upon oxidation, will yield the disclosed quantities of NiO described herein.

In some embodiments, the catalysts comprising an oxide of nickel, an oxide of molybdenum, and a support can comprise from 0.5 wt. % to 10 wt. % of an oxide of nickel. In other embodiments, the catalysts comprising an oxide of nickel, an oxide of molybdenum, and a support can comprise from 1 wt. % to 7 wt. % of an oxide of nickel; or alternatively, from 2 wt. % to 5 wt. % of an oxide of nickel. In other embodiments, the catalysts comprise an oxide of nickel, an oxide of molybdenum, and a support can comprise from 8 wt. % to 35 wt. % $MoO_3$, from 0.5 wt. % to 10 wt. % NiO, and from 55 wt. % to 91.5 wt. % alumina; alternatively, from 8 wt. % to 35 wt. % $MoO_3$, from 1 wt. % to 7 wt. % NiO, and from 58 wt. % to 91 wt. % alumina; alternatively, from 15 wt. % to 30 wt. % $MoO_3$, from 2 wt. % to 5 wt. % NiO, and from 65 wt. % to 83 wt. % alumina; alternatively, from 10 wt. % to 20 wt. % $MoO_3$, from 2 wt. % to 5 wt. % NiO, and from 75 wt. % to 88 wt. % alumina; or alternatively, from 8 wt. % to 15 wt. % $MoO_3$, from 2 wt. % to 5 wt. % NiO, and from 80 wt. % to 90 wt. % alumina. In further embodiments, the catalysts can also contain from 0.05 wt. % to 1 wt. % $Na_2O$. In yet other embodiments, the catalysts can also contain up to 0.05 wt. % iron. In embodiments in which the catalysts also contain iron, the iron can be present as elemental iron or as an oxide.

In an aspect, the first, second, and third catalysts A, B, C, comprise an oxide of molybdenum and an oxide of nickel supported on alumina. In some aspects, the first, second, and third catalysts A, B, C comprise about 0.5 wt. % to about 5 wt. % nickel monoxide (NiO), about 3 wt. % to about 30 wt. % molybdenum trioxide ($Mo_2O_3$), and about 50 wt. % to about 95 wt. % alumina. In another aspect, the second and third catalysts B, C further comprise about 2 wt. % to about 10 wt. % aluminium phosphate ($Al_3(PO_4)_2$), which is an activity promoter, as shown in Table 1.

TABLE 1

| Component | Catalyst A | Catalyst B | Catalyst C |
|---|---|---|---|
| NiO, wt. % | 0.5-5 | 1-3 | 1-5 |
| $Mo_2O_3$, wt. % | 3-10 | 5-15 | 20-30 |
| Alumina, wt. % | 75-95 | 70-90 | 50-70 |
| $Al_3(PO_4)_2$, wt. % | | 2-8 | 5-10 |

While not wishing to be bound by theory, it is believed that amount of $Mo_2O_3$ is directly proportional to the catalyst activity. The higher the amount of $Mo_2O_3$, the higher the activity for converting methanol 8 to methyl mercaptan 18. In an aspect, catalyst B has more $Mo_2O_3$ than catalyst A and catalyst C has more $Mo_2O_3$ than catalyst B.

Supports suitable for use as a carrier for the metal component(s) of the hydrotreating catalysts A, B, C include any material that is inert to the reaction conditions. Some suitable supports include activated carbon, alumina, zirconia, thoria, pumice, silica, and silica-alumina. In some embodiments, the support is alumina. In other embodiments, the support is a gamma (γ)-alumina. Generally, the support comprises from 50 wt. % to 90 wt. % of the catalyst composition. Alternatively, the support can comprise from 50 wt. % to 70 wt. % of the catalyst composition; alternatively, from 60 wt. % to 85 wt. % of the catalyst composition; or alternatively, from 70 wt. % to 80 wt. % of the catalyst composition.

In an aspect, the first catalyst A comprises about 0.5 wt. % to about 5 wt. % nickel monoxide, about 3 wt. % to about 10 wt. % molybdenum trioxide, and about 75 wt. % to about 95 wt. % alumina. In an aspect, the second catalyst B comprises about 1 wt. % to about 3 wt. % nickel monoxide, about 5 wt. % to about 15 wt. % molybdenum trioxide, about 70 wt. % to about 90 wt. % alumina, and about 2 wt. % to about 8 wt. % aluminium phosphate. In an aspect, the third catalyst C comprises about 1 wt. % to about 5 wt. % nickel monoxide, about 20 wt. % to about 30 wt. % molybdenum trioxide, about 50 wt. % to about 70 wt. % alumina, and about 5 wt. % to about 10 wt. % aluminium phosphate. In general, the catalysts A, B, and C are referred to as hydrotreating catalysts. A suitable hydrotreating catalyst that can be used as catalyst A can be obtained commercially from Haldor Topsoe, Inc. as TK-711. A suitable hydrotreating catalyst that can be used as catalyst B can be obtained commercially from Haldor Topsoe, Inc. as TK-751. A suitable hydrotreating catalyst that can be used as catalyst C can be obtained commercially from Haldor Topsoe, Inc. as TK-753. Another suitable catalyst that can be used as catalyst C can be obtained commercially from Akzo Nobel as KF-757, however, if used, pre-sulfiding the graded catalyst bed 5 would be required.

The first, second, and third catalysts can have any shape useful in the present invention. In an aspect, the first, second, and third catalysts have a trilobe shape. In an aspect, the first, second, and third catalysts have a spherical shape. Suitable shapes will be apparent to those of skill in the art and are to be considered within the scope of the present invention.

In some embodiments, the hydrotreating catalysts A, B, C are partially or completely sulfided prior to use. Alternatively, the hydrotreating catalysts A, B, C can be employed directly in the oxide form because sulfiding occurs in the presence of $H_2S$ under the reaction conditions.

As shown in FIG. 1, each of the catalysts A, B, C can be located in a single catalyst bed or in a series of catalyst beds or zones 12, 14, 16. Although only three catalyst beds are shown in FIG. 1 and are described herein, any number of catalyst beds can be used to form the graded catalyst blend 5. In an aspect, each catalyst bed can have an equal amount of material contained therein. In another aspect, the catalyst beds can have varying volumes of material contained therein. As used herein, the term "bed" describes sections of a reactor that contain a different catalyst component than a previous section of the reactor. Catalyst beds do not require a physical barrier to separate each bed. A physical barrier can be used to separate each bed, if desired. For example, a separate reactor vessel can be used to separate each catalyst bed. When there is not a physical barrier present, eventually the different catalysts A, B, C in each of the beds 12, 14, 16 can intermingle to become a continuum along the reactor vessel.

As used herein, the term "near isothermal" is defined as maintaining an operating temperature across the graded catalyst bed 5 within a 5° C. differential across the graded catalyst bed 5. In other words, the operating temperature of the graded catalyst bed 5 is maintained within +/−5° C. of an inlet operating temperature of the graded catalyst bed 5. The reaction of the methanol 8 with the hydrogen sulfide 10 in the presence of the catalysts A, B, C is an exothermic reaction. External counter-current cooling water can be used, but is not required, to remove the heat generated from the reaction within each of the catalyst beds or zones 12, 14, 16. Because catalyst A has a lower activity for converting methanol to methyl mercaptan than the second and third catalysts B, less heat is generated within the catalyst bed or zone 12. In prior attempts of producing methyl mercaptan from methanol using a catalyst, a "hot spot" can develop toward the inlet of the catalyst bed if high conversion of methanol was desired. The "hot spot," which usually occurred about 290° C., would cause excessive light gases, such as $CO_2$, $CH_4$, and $H_2$, to be produced. The "hot spot" would also reduce the activity of the catalyst bed and decrease the efficiency of the reaction. By maintaining near isothermal conditions across the entire graded catalyst bed 5, the amount of light gases emitted is significantly reduced, the catalyst bed lasts longer, and the efficiency of the reaction is substantially increased. Diluting the catalyst by using a lower activity catalyst at the inlet of the graded catalyst bed 5 essentially eliminates the "hot spot" that developed in traditional catalyst beds.

While not wishing to be bound by theory, it is believed that having a lower activity catalyst at the beginning of the catalyst bed reduces the chance of reactor hot spots occurring by reducing conversion and the amount of heat produced by the reaction.

In an aspect, the near isothermal conditions are at least partially maintained by providing an external cooling means, such as an external counter-current cooling water exchanger, for the graded catalyst bed 5. Alternatively, a co-current cooling water exchanger can be used. Other suitable cooling means will be apparent to those of skill in the art and are to be considered within the scope of the present invention. In prior art processes, co-current external cooling water exchangers have been used. Because the inlet of the catalyst bed had such a large amount of heat being discharged, the temperature of the cooling water was increased, which provided less cooling capabilities as the cooling water proceeded to the downstream portions of the catalyst bed 5. With the graded catalyst bed 5 process, more heat removal is needed at the outlet of the graded catalyst bed 5. By using counter-current flow, the cooling water has the greatest cooling capacity when the cooling water reaches the hottest part of the graded catalyst bed 5. Using counter-current flow performs well, but co-current flow is sufficient.

Besides the "hot spot" formation, other problems have occurred in prior art attempts of producing mercaptans from alcohols, such as catalyst poisoning. To prevent poisoning the graded catalyst bed 5 in embodiments of the present invention, the processes described herein can also include supplying a sulfur source to the graded catalyst bed 5 prior to supplying the methanol 8 and hydrogen sulfide 10 to the graded catalyst bed 5. The sulfur source is used to "pre-sulfide" the graded catalyst bed 5 prior to introduction of the feedstreams. Suitable sulfur sources, such as hydrogen sulfide, will be apparent to those of skill in the art and are to be considered within the scope of the present invention.

As another embodiment of the present invention, a process for selective production of methyl mercaptan is provided. In this embodiment, methanol 8 and hydrogen sulfide 10 are contacted with a graded catalyst bed 5 comprising at least three catalysts, A, B, C. The first catalyst A has a lower activity for converting methanol to the methyl mercaptan than the second and the third catalysts B, C. The second catalyst B has a lower activity for converting methanol to the methyl mercaptan than the third catalyst C. The first catalyst A is located upstream of the second catalyst B. The second catalyst B is located upstream of the third catalyst C. The methanol 8 and the hydrogen sulfide 10 are reacted to produce a reactor effluent comprising the methyl mercaptan 18 while maintaining near isothermal conditions during reaction of the methanol 8 and the hydrogen sulfide 10. In an aspect, the product comprises less than about 20 wt. % dimethyl sulfide.

In another aspect, the product comprises less than about 20 wt. % decomposition reaction products.

As another embodiment of the present invention, a graded catalyst bed 5 is provided. In this embodiment, the graded catalyst bed 5 includes a first catalyst A, a second catalyst B, and a third catalyst C. The first catalyst A comprises nickel or cobalt oxide, molybdenum trioxide, and alumina and has a bulk density greater than about 37 lbs/ft$^3$. The second catalyst B comprises nickel or cobalt oxide, molybdenum trioxide, alumina, and aluminium phosphate and has a bulk density greater than about 38 lbs/ft$^3$. The third catalyst C comprises nickel or cobalt oxide, molybdenum trioxide, alumina, and aluminium phosphate and has a bulk density greater than about 51 lbs/ft$^3$. The first, second, and third catalysts A, B, C can be used to produce methyl mercaptan by reacting methanol 8 with hydrogen sulfide 10, in the presence of the graded catalyst bed 5 while maintaining near isothermal conditions, to produce the methyl mercaptan 18. Generally, the methyl mercaptan 18 can be produced in one process pass.

In some embodiments, the graded catalyst bed 5 comprises about 20% to about 35% of the first catalyst A, about 20% to about 35% of the second catalyst B, and from about 35% to about 55% of the third catalyst C.

EXAMPLE

As shown in FIG. 1, methanol 8 was converted to methyl mercaptan 18 in a fixed bed catalytic flow reactor in downflow using a graded catalyst bed 5. The catalyst that was used in this example was a catalyst blend 5 of three NiMo catalysts. The hydrotreating catalyst A was produced by Haldor Topsoe Inc. and is commercially available as TK-711. The hydrotreating catalyst B was produced by Haldor Topsoe Inc. and is commercially available as TK-751. The hydrotreating catalyst C was produced by Haldor Topsoe Inc. and is commercially available as TK-573.

The graded catalyst bed 5 was packed in the reactor in three zones by volume. The first zone 12 contained 25 vol. % of the graded catalyst bed 5 and contained catalyst A, the second zone 14 contained 25 vol. % of the graded catalyst bed 5 and contained catalyst B, and the third zone 16 contained 50 vol. % of the graded catalyst bed 5 and contained catalyst C. The results of the synthesis of methyl mercaptan using this particular graded catalyst bed 5 are included in Tables 2-4.

TABLE 2

| Sample Number | Catalyst grams | H$_2$S/MeOH mole ratio | Press psig | LHSV | Inlet T °C. | Mid T °C. | Outlet T °C. | WAT °C. | CO$_2$ Mol % | H$_2$S Mol % | H$_2$O Mol % | DME Mol % |
|---|---|---|---|---|---|---|---|---|---|---|---|---|
| TK711, TK751&TK573 53.4 ml catalyst Cat Pack 422-30 53.4 ml catalyst | | | | | | | | | | | | |
| Feed | | | | | | | | | | | | |
| 1 | 41.63 | 9.0 | 450 | 0.25 | 190 | 190 | 190 | 190.0 | 0.00 | 91.28 | 1.24 | 0.08 |
| 2 | 41.63 | 9.0 | 450 | 0.25 | 190 | 190 | 190 | 190.0 | 0.00 | 90.91 | 1.19 | 0.08 |
| 3 | 41.63 | 9.0 | 450 | 0.25 | 190 | 190 | 190 | 190.0 | 0.00 | 91.06 | 1.19 | 0.10 |
| 4 | 41.63 | 9.0 | 450 | 0.25 | 200 | 201 | 200 | 200.3 | 0.00 | 91.07 | 1.22 | 0.09 |
| 5 | 41.63 | 9.0 | 450 | 0.25 | 200 | 200 | 200 | 200.0 | 0.00 | 90.74 | 0.99 | 0.10 |
| 6 | 41.63 | 9.0 | 450 | 0.25 | 200 | 200 | 200 | 200.0 | 0.00 | 91.69 | 0.96 | 0.10 |
| 7 | 41.63 | 9.0 | 450 | 0.25 | 210 | 210 | 210 | 210.0 | 0.02 | 90.41 | 0.90 | 0.11 |
| 8 | 41.63 | 9.0 | 450 | 0.25 | 210 | 210 | 210 | 210.0 | 0.02 | 90.35 | 0.91 | 0.11 |
| 9 | 41.63 | 9.0 | 450 | 0.25 | 210 | 210 | 210 | 210.0 | 0.03 | 90.45 | 0.78 | 0.11 |
| 10 | 41.63 | 9.0 | 450 | 0.25 | 220 | 220 | 220 | 220.0 | 0.04 | 90.54 | 0.78 | 0.11 |
| 11 | 41.63 | 9.0 | 450 | 0.25 | 220 | 220 | 220 | 220.0 | 0.04 | 89.94 | 0.82 | 0.11 |
| 12 | 41.63 | 9.0 | 450 | 0.25 | 220 | 220 | 220 | 220.0 | 0.05 | 90.68 | 0.70 | 0.10 |
| 13 | 41.63 | 9.0 | 450 | 0.25 | 231 | 230 | 230 | 230.3 | 0.06 | 90.16 | 0.73 | 0.09 |
| 14 | 41.63 | 9.0 | 450 | 0.25 | 229 | 230 | 230 | 229.7 | 0.06 | 90.22 | 0.85 | 0.07 |
| 15 | 41.63 | 9.0 | 450 | 0.25 | 229 | 230 | 230 | 229.7 | 0.07 | 90.65 | 0.68 | 0.07 |
| 16 | 41.63 | 9.0 | 450 | 0.25 | 240 | 240 | 240 | 240.0 | 0.10 | 90.86 | 0.88 | 0.04 |
| 17 | 41.63 | 9.0 | 450 | 0.25 | 238 | 240 | 240 | 239.3 | 0.13 | 91.84 | 0.68 | 0.03 |
| 18 | 41.63 | 9.0 | 450 | 0.25 | 240 | 240 | 240 | 240.0 | 0.11 | 90.60 | 0.67 | 0.03 |
| 19 | 41.63 | 6.0 | 450 | 0.25 | 190 | 190 | 190 | 190.0 | 0.00 | 87.71 | 1.38 | 0.10 |
| 20 | 41.63 | 6.0 | 450 | 0.25 | 190 | 190 | 190 | 190.0 | 0.00 | 88.05 | 1.40 | 0.12 |
| 21 | 41.63 | 6.0 | 450 | 0.25 | 190 | 190 | 190 | 190.0 | 0.00 | 88.08 | 1.42 | 0.10 |
| 22 | 41.63 | 6.0 | 450 | 0.25 | 199 | 200 | 200 | 199.7 | 0.00 | 86.95 | 1.60 | 0.11 |
| 23 | 41.63 | 6.0 | 450 | 0.25 | 199 | 200 | 200 | 199.7 | 0.02 | 87.17 | 1.39 | 0.12 |
| 24 | 41.63 | 6.0 | 450 | 0.25 | 199 | 200 | 200 | 199.7 | 0.02 | 87.68 | 1.20 | 0.12 |
| 25 | 41.63 | 6.0 | 450 | 0.25 | 209 | 210 | 211 | 210.0 | 0.02 | 87.10 | 1.31 | 0.14 |
| 26 | 41.63 | 6.0 | 450 | 0.25 | 209 | 210 | 211 | 210.0 | 0.03 | 86.56 | 1.21 | 0.15 |
| 27 | 41.63 | 6.0 | 450 | 0.25 | 209 | 210 | 211 | 210.0 | 0.03 | 86.41 | 1.06 | 0.15 |
| 28 | 41.63 | 6.0 | 450 | 0.25 | 220 | 221 | 220 | 220.3 | 0.05 | 86.73 | 0.97 | 0.17 |
| 29 | 41.63 | 6.0 | 450 | 0.25 | 219 | 220 | 220 | 219.7 | 0.05 | 85.82 | 0.98 | 0.16 |
| 30 | 41.63 | 6.0 | 450 | 0.25 | 232 | 231 | 230 | 231.0 | 0.08 | 86.38 | 0.96 | 0.15 |
| 31 | 41.63 | 6.0 | 450 | 0.25 | 229 | 230 | 230 | 229.7 | 0.10 | 86.98 | 0.82 | 0.15 |
| 32 | 41.63 | 6.0 | 450 | 0.25 | 229 | 230 | 230 | 229.7 | 0.10 | 86.99 | 0.81 | 0.13 |
| 33 | 41.63 | 6.0 | 450 | 0.25 | 240 | 240 | 240 | 240.0 | 0.12 | 86.87 | 0.90 | 0.10 |

TABLE 2-continued

| | | | | | | | | | | | |
|---|---|---|---|---|---|---|---|---|---|---|---|
| 34 | 41.63 | 6.0 | 450 | 0.25 | 239 | 240 | 240 | 239.7 | 0.15 | 87.41 | 0.74 | 0.08 |
| 35 | 41.63 | 6.0 | 450 | 0.25 | 239 | 240 | 240 | 239.7 | 0.16 | 87.75 | 0.70 | 0.07 |

| Sample Number | MeOH Mol % | MeSH Mol % | DMS Mol % | DMDS Mol % | MeOH Conversion % | MeSH Conversion % | MeSH Productivity % | Light Gas Conversion % | DMS Conversion % |
|---|---|---|---|---|---|---|---|---|---|
| | TK711, TK751&TK573 53.4 ml catalyst Cat Pack 422-30 53.4 ml catalyst | | | | | | | | |
| | Feed | | | | | | | | |
| 1 | 1.25 | 5.97 | 0.11 | 0.07 | 83.46 | 91.98 | 76.76 | 0.00 | 3.33 |
| 2 | 1.84 | 5.79 | 0.11 | 0.07 | 75.61 | 91.57 | 69.24 | 0.00 | 3.47 |
| 3 | 1.89 | 5.58 | 0.12 | 0.06 | 74.97 | 91.10 | 68.30 | 0.00 | 3.78 |
| 4 | 1.80 | 5.64 | 0.13 | 0.04 | 76.14 | 91.52 | 69.68 | 0.00 | 4.29 |
| 5 | 1.36 | 6.61 | 0.16 | 0.04 | 82.02 | 91.68 | 75.20 | 0.00 | 4.51 |
| 6 | 1.03 | 6.05 | 0.15 | 0.03 | 86.39 | 91.66 | 79.18 | 0.00 | 4.48 |
| 7 | 0.97 | 7.35 | 0.22 | 0.04 | 87.21 | 90.47 | 78.90 | 0.49 | 5.31 |
| 8 | 0.75 | 7.60 | 0.24 | 0.04 | 90.04 | 90.25 | 81.26 | 0.56 | 5.62 |
| 9 | 0.59 | 7.79 | 0.25 | 0.04 | 92.25 | 90.22 | 83.23 | 0.61 | 5.80 |
| 10 | 0.38 | 7.86 | 0.30 | 0.03 | 94.96 | 89.18 | 84.69 | 0.81 | 6.71 |
| 11 | 0.37 | 8.37 | 0.35 | 0.04 | 95.08 | 88.66 | 84.30 | 0.80 | 7.40 |
| 12 | 0.21 | 7.94 | 0.33 | 0.03 | 97.15 | 88.61 | 86.09 | 1.05 | 7.41 |
| 13 | 0.12 | 8.44 | 0.43 | 0.03 | 98.42 | 87.43 | 86.05 | 1.20 | 8.82 |
| 14 | 0.08 | 8.28 | 0.47 | 0.03 | 99.00 | 86.66 | 85.79 | 1.33 | 9.93 |
| 15 | 0.05 | 8.05 | 0.47 | 0.02 | 99.29 | 86.28 | 85.66 | 1.55 | 10.14 |
| 16 | 0.03 | 7.61 | 0.56 | 0.02 | 99.66 | 84.13 | 83.85 | 2.14 | 12.32* |
| 17 | 0.03 | 6.87 | 0.54 | 0.01 | 99.63 | 82.71 | 82.40 | 2.12 | 13.10 |
| 18 | 0.02 | 7.99 | 0.67 | 0.02 | 99.79 | 82.84 | 82.67 | 2.21 | 13.95 |
| 19 | 2.11 | 8.26 | 0.42 | 0.02 | 81.20 | 88.34 | 71.73 | 0.00 | 9.07 |
| 20 | 2.60 | 7.48 | 0.34 | 0.02 | 76.80 | 88.69 | 68.11 | 0.00 | 8.10 |
| 21 | 2.85 | 7.22 | 0.31 | 0.02 | 74.54 | 89.34 | 66.59 | 0.00 | 7.73 |
| 22 | 3.25 | 7.72 | 0.35 | 0.03 | 71.02 | 88.90 | 63.14 | 0.00 | 8.03 |
| 23 | 2.56 | 8.32 | 0.40 | 0.03 | 77.12 | 88.07 | 67.92 | 0.36 | 8.46 |
| 24 | 2.14 | 8.42 | 0.40 | 0.03 | 80.86 | 88.14 | 71.27 | 0.36 | 8.42 |
| 25 | 1.91 | 9.02 | 0.48 | 0.03 | 82.93 | 87.04 | 72.19 | 0.41 | 9.18 |
| 26 | 1.68 | 9.80 | 0.57 | 0.03 | 85.01 | 86.20 | 73.28 | 0.53 | 9.97 |
| 27 | 1.64 | 10.12 | 0.59 | 0.03 | 85.40 | 86.29 | 73.69 | 0.52 | 10.13 |
| 28 | 1.02 | 10.39 | 0.68 | 0.03 | 90.90 | 84.80 | 77.09 | 0.78 | 11.08 |
| 29 | 0.82 | 11.35 | 0.83 | 0.03 | 92.67 | 84.13 | 77.96 | 0.78 | 12.23 |
| 30 | 0.38 | 11.17 | 0.93 | 0.03 | 96.64 | 82.43 | 79.65 | 1.17 | 13.79 |
| 31 | 0.24 | 10.80 | 0.99 | 0.02 | 97.90 | 81.13 | 79.43 | 1.47 | 14.82 |
| 32 | 0.17 | 10.83 | 1.03 | 0.02 | 98.45 | 80.81 | 79.56 | 1.52 | 15.38 |
| 33 | 0.10 | 10.76 | 1.25 | 0.02 | 99.14 | 78.25 | 77.57 | 1.80 | 18.21 |
| 34 | 0.05 | 10.39 | 1.31 | 0.02 | 99.51 | 77.00 | 76.63 | 2.17 | 19.37 |
| 35 | 0.04 | 10.12 | 1.31 | 0.01 | 99.66 | 76.45 | 76.19 | 2.45 | 19.86* |

MeOH: methanol, $CH_4O$;
MeSH: methyl mercaptan or methanethiol, $CH_4S$;
DME: dimethyl ether, $C_2H_6O$;
DMS: dimethyl sulfide, $C_2H_6S$;
DMDS: dimethyl disulfide, $C_2H_6S_2$;
LHSV: liquid hourly space velocity;
WAT: weight average temperature

TABLE 3

| Sample Number | Catalyst grams | $H_2S$/MeOH mole ratio | Press psig | LHSV | Inlet T ° C. | Mid T ° C. | Outlet T ° C. | WAT ° C. | $CO_2$ Mol % | $H_2S$ Mol % | $H_2O$ Mol % | DME Mol % |
|---|---|---|---|---|---|---|---|---|---|---|---|---|
| | TK711, TK751&TK573 53.4 ml catalyst Cat Pack 422-31 | | | | | | | | | | | |
| | feed | | | | | | | | | | | |
| 1 | 41.45 | 6.0 | 450 | 0.25 | 190 | 190 | 190 | 190.0 | 0.00 | 85.98 | 2.21 | 0.15 |
| 2 | 41.45 | 6.0 | 450 | 0.25 | 189 | 190 | 190 | 189.7 | 0.02 | 87.97 | 1.54 | 0.13 |
| 3 | 41.45 | 6.0 | 450 | 0.25 | 200 | 201 | 200 | 200.3 | 0.00 | 86.43 | 1.80 | 0.12 |
| 4 | 41.45 | 6.0 | 450 | 0.25 | 199 | 200 | 200 | 199.7 | 0.02 | 85.86 | 1.63 | 0.15 |
| 5 | 41.45 | 6.0 | 450 | 0.25 | 199 | 200 | 200 | 199.7 | 0.03 | 86.96 | 1.37 | 0.15 |
| 6 | 41.45 | 6.0 | 450 | 0.25 | 210 | 210 | 211 | 210.3 | 0.03 | 86.43 | 1.26 | 0.16 |
| 7 | 41.45 | 6.0 | 450 | 0.25 | 210 | 210 | 210 | 210.0 | 0.04 | 86.19 | 1.15 | 0.18 |
| 8 | 41.45 | 6.0 | 450 | 0.25 | 210 | 210 | 210 | 210.0 | 0.05 | 86.53 | 1.05 | 0.17 |
| 9 | 41.45 | 6.0 | 450 | 0.25 | 220 | 220 | 220 | 220.0 | 0.05 | 86.30 | 0.96 | 0.18 |
| 10 | 41.45 | 6.0 | 450 | 0.25 | 220 | 220 | 220 | 220.0 | 0.07 | 86.27 | 0.91 | 0.19 |
| 11 | 41.45 | 6.0 | 450 | 0.25 | 220 | 220 | 220 | 220.0 | 0.08 | 86.53 | 0.84 | 0.17 |
| 12 | 41.45 | 6.0 | 450 | 0.25 | 230 | 230 | 229 | 229.7 | 0.08 | 85.63 | 1.09 | 0.17 |
| 13 | 41.45 | 6.0 | 450 | 0.25 | 230 | 230 | 230 | 230.0 | 0.10 | 86.06 | 0.96 | 0.17 |

TABLE 3-continued

| | | | | | | | | | | | | |
|---|---|---|---|---|---|---|---|---|---|---|---|---|
| 14 | 41.45 | 6.0 | 450 | 0.25 | 230 | 230 | 230 | 230.0 | 0.12 | 86.66 | 0.76 | 0.16 |
| 15 | 41.45 | 6.0 | 450 | 0.25 | 240 | 240 | 240 | 240.0 | 0.16 | 86.97 | 0.91 | 0.13 |
| 16 | 41.45 | 6.0 | 450 | 0.25 | 239 | 240 | 240 | 239.7 | 0.17 | 87.04 | 0.67 | 0.10 |
| 17 | 41.45 | 6.0 | 450 | 0.25 | 239 | 240 | 240 | 239.7 | 0.17 | 86.62 | 1.20 | 0.11 |
| 18 | 41.45 | 9.0 | 450 | 0.25 | 189 | 191 | 190 | 190.0 | 0.00 | 88.99 | 1.57 | 0.08 |
| 19 | 41.45 | 9.0 | 450 | 0.25 | 189 | 190 | 190 | 189.7 | 0.00 | 91.43 | 1.19 | 0.07 |
| 20 | 41.45 | 9.0 | 450 | 0.25 | 199 | 200 | 201 | 200.0 | 0.00 | 90.65 | 1.29 | 0.06 |
| 21 | 41.45 | 9.0 | 450 | 0.25 | 199 | 200 | 200 | 199.7 | 0.00 | 90.17 | 1.16 | 0.07 |
| 22 | 41.45 | 9.0 | 450 | 0.25 | 199 | 200 | 200 | 199.7 | 0.00 | 90.67 | 1.07 | 0.08 |
| 23 | 41.45 | 9.0 | 450 | 0.25 | 210 | 211 | 210 | 210.3 | 0.02 | 90.31 | 1.08 | 0.09 |
| 24 | 41.45 | 9.0 | 450 | 0.25 | 209 | 210 | 210 | 209.7 | 0.02 | 89.36 | 1.04 | 0.08 |
| 25 | 41.45 | 9.0 | 450 | 0.25 | 209 | 210 | 210 | 209.7 | 0.03 | 91.31 | 0.90 | 0.07 |
| 26 | 41.45 | 9.0 | 450 | 0.25 | 220 | 220 | 220 | 220.0 | 0.03 | 91.15 | 0.91 | 0.09 |
| 27 | 41.45 | 9.0 | 450 | 0.25 | 220 | 220 | 220 | 220.0 | 0.04 | 91.42 | 0.78 | 0.07 |
| 28 | 41.45 | 9.0 | 450 | 0.25 | 220 | 220 | 220 | 220.0 | 0.05 | 91.45 | 0.72 | 0.07 |
| 29 | 41.45 | 9.0 | 450 | 0.25 | 230 | 229 | 228 | 229.0 | 0.07 | 91.27 | 0.89 | 0.06 |
| 30 | 41.45 | 9.0 | 450 | 0.25 | 232 | 230 | 230 | 230.7 | 0.07 | 91.20 | 0.78 | 0.05 |
| 31 | 41.45 | 9.0 | 450 | 0.25 | 231 | 230 | 230 | 230.3 | 0.08 | 91.81 | 0.68 | 0.04 |
| 32 | 41.45 | 9.0 | 450 | 0.25 | 240 | 240 | 240 | 240.0 | 0.09 | 91.09 | 0.80 | 0.03 |
| 33 | 41.45 | 9.0 | 450 | 0.25 | 239 | 240 | 240 | 239.7 | 0.10 | 91.39 | 0.78 | 0.02 |

| Sample Number | MeOH Mol % | MeSH Mol % | DMS Mol % | DMDS Mol % | MeOH Conversion % | MeSH Conversion % | MeSH Productivity % | Light Gas Conversion % | DMS Conversion % |
|---|---|---|---|---|---|---|---|---|---|
| | TK711, TK751&TK573 53.4 ml catalyst Cat Pack 422-31 | | | | | | | | |
| | feed | | | | | | | | |
| 1 | 3.58 | 7.75 | 0.14 | 0.20 | 68.05 | 88.82 | 60.44 | 0.00 | 3.16 |
| 2 | 3.47 | 6.65 | 0.13 | 0.10 | 69.05 | 89.71 | 61.94 | 0.48 | 3.61 |
| 3 | 3.85 | 7.54 | 0.17 | 0.09 | 65.66 | 90.84 | 59.65 | 0.00 | 4.19 |
| 4 | 3.23 | 8.79 | 0.25 | 0.09 | 71.17 | 89.49 | 63.69 | 0.49 | 5.10 |
| 5 | 2.58 | 8.62 | 0.25 | 0.07 | 76.96 | 89.68 | 69.02 | 0.56 | 5.12 |
| 6 | 2.13 | 9.62 | 0.32 | 0.07 | 80.96 | 89.16 | 72.18 | 0.61 | 5.99 |
| 7 | 1.88 | 10.14 | 0.39 | 0.07 | 83.19 | 88.25 | 73.42 | 0.75 | 6.79 |
| 8 | 1.54 | 10.25 | 0.40 | 0.06 | 86.25 | 88.34 | 76.20 | 0.79 | 6.86 |
| 9 | 1.10 | 10.90 | 0.50 | 0.06 | 90.14 | 87.29 | 78.68 | 0.87 | 8.00 |
| 10 | 0.91 | 11.08 | 0.59 | 0.05 | 91.84 | 86.03 | 79.01 | 1.13 | 9.13 |
| 11 | 0.74 | 11.06 | 0.61 | 0.05 | 93.39 | 85.82 | 80.16 | 1.24 | 9.52 |
| 12 | 0.52 | 11.76 | 0.79 | 0.05 | 95.38 | 84.37 | 80.47 | 1.20 | 11.29 |
| 13 | 0.41 | 11.50 | 0.87 | 0.04 | 96.38 | 83.00 | 80.00 | 1.50 | 12.51 |
| 14 | 0.31 | 11.19 | 0.89 | 0.04 | 97.26 | 82.31 | 80.05 | 1.74 | 13.05 |
| 15 | 0.19 | 10.65 | 1.12 | 0.03 | 98.30 | 78.72 | 77.38 | 2.35 | 16.63 |
| 16 | 0.12 | 10.78 | 1.26 | 0.03 | 98.91 | 77.56 | 76.72 | 2.47 | 18.19* |
| 17 | 0.10 | 10.67 | 1.29 | 0.02 | 99.14 | 77.11 | 76.44 | 2.49 | 18.57 |
| 18 | 3.48 | 5.66 | 0.21 | 0.01 | 46.47 | 90.51 | 42.06 | 0.00 | 6.77 |
| 19 | 2.16 | 4.97 | 0.17 | 0.01 | 66.71 | 90.82 | 60.59 | 0.00 | 6.38 |
| 20 | 2.37 | 5.41 | 0.20 | 0.02 | 63.54 | 90.71 | 57.64 | 0.00 | 6.70 |
| 21 | 1.94 | 6.39 | 0.25 | 0.02 | 70.14 | 90.33 | 63.36 | 0.00 | 7.14 |
| 22 | 1.60 | 6.32 | 0.24 | 0.02 | 75.40 | 90.26 | 68.06 | 0.00 | 6.94 |
| 23 | 1.41 | 6.77 | 0.29 | 0.02 | 78.23 | 88.85 | 69.50 | 0.57 | 7.72 |
| 24 | 1.25 | 7.87 | 0.35 | 0.02 | 80.71 | 89.09 | 71.90 | 0.54 | 7.96 |
| 25 | 0.82 | 6.57 | 0.28 | 0.02 | 87.34 | 89.28 | 77.98 | 0.74 | 7.51 |
| 26 | 0.60 | 6.88 | 0.32 | 0.02 | 90.79 | 88.25 | 80.13 | 0.89 | 8.17 |
| 27 | 0.38 | 6.95 | 0.34 | 0.02 | 94.20 | 88.13 | 83.02 | 1.11 | 8.52 |
| 28 | 0.31 | 7.05 | 0.34 | 0.02 | 95.24 | 87.99 | 83.80 | 1.23 | 8.57 |
| 29 | 0.17 | 7.10 | 0.43 | 0.01 | 97.33 | 86.30 | 84.00 | 1.63 | 10.38 |
| 30 | 0.13 | 7.31 | 0.45 | 0.01 | 97.98 | 86.24 | 84.50 | 1.62 | 10.72 |
| 31 | 0.09 | 6.88 | 0.41 | 0.01 | 98.61 | 86.27 | 85.08 | 2.00 | 10.35 |
| 32 | 0.05 | 7.40 | 0.53 | 0.01 | 99.26 | 84.77 | 84.15 | 2.13 | 12.13* |
| 33 | 0.03 | 7.09 | 0.58 | 0.01 | 99.60 | 83.33 | 83.00 | 2.38 | 13.64 |

TABLE 4

| Sample Number | Catalyst grams | H$_2$S/MeOH mole ratio | Press psig | LHSV | Inlet T ° C. | Mid T ° C. | Outlet T ° C. | WAT ° C. | CO$_2$ Mol % | H$_2$S Mol % | H$_2$O Mol % | DME Mol % |
|---|---|---|---|---|---|---|---|---|---|---|---|---|
| | TK711, TK751, TK773 53 ml catalyst | | | | | | | | | | | |
| | feed | | | | | | | | | | | |
| 1 | 53 | 9.0 | 450 | 0.14 | 189 | 190 | 190 | 189.7 | 0.00 | 91.02 | 1.24 | 0.06 |
| 2 | 53 | 9.0 | 450 | 0.14 | 189 | 190 | 190 | 189.7 | 0.00 | 91.21 | 1.21 | 0.06 |
| 3 | 53 | 9.0 | 450 | 0.14 | 190 | 190 | 189 | 189.7 | 0.00 | 89.69 | 3.84 | 0.06 |
| 4 | 53 | 9.0 | 450 | 0.14 | 200 | 201 | 200 | 200.3 | 0.00 | 91.14 | 1.24 | 0.06 |
| 5 | 53 | 9.0 | 450 | 0.14 | 200 | 201 | 200 | 200.3 | 0.02 | 87.82 | 4.45 | 0.10 |
| 6 | 53 | 9.0 | 450 | 0.14 | 200 | 201 | 200 | 200.3 | 0.02 | 91.83 | 0.79 | 0.07 |

TABLE 4-continued

| | | | | | | | | | | | | |
|---|---|---|---|---|---|---|---|---|---|---|---|---|
| 7 | 53 | 9.0 | 450 | 0.14 | 210 | 210 | 210 | 210.0 | 0.03 | 92.05 | 1.71 | 0.07 |
| 8 | 53 | 9.0 | 450 | 0.14 | 209 | 210 | 210 | 209.7 | 0.04 | 89.38 | 3.23 | 0.08 |
| 9 | 53 | 9.0 | 450 | 0.14 | 210 | 211 | 210 | 210.3 | 0.05 | 91.80 | 0.97 | 0.07 |
| 10 | 53 | 9.0 | 450 | 0.14 | 221 | 221 | 220 | 220.7 | 0.06 | 90.69 | 2.00 | 0.07 |
| 11 | 53 | 9.0 | 450 | 0.14 | 220 | 220 | 221 | 220.3 | 0.08 | 92.02 | 0.70 | 0.06 |
| 12 | 53 | 9.0 | 450 | 0.14 | 220 | 220 | 220 | 220.0 | 0.09 | 89.86 | 4.00 | 0.07 |
| 13 | 53 | 9.0 | 450 | 0.14 | 229 | 230 | 230 | 229.7 | 0.11 | 91.69 | 0.79 | 0.00 |
| 14 | 53 | 9.0 | 450 | 0.14 | 230 | 230 | 230 | 230.0 | 0.10 | 91.39 | 0.78 | 0.05 |
| 15 | 53 | 9.0 | 450 | 0.14 | 229 | 230 | 230 | 229.7 | 0.13 | 91.93 | 0.68 | 0.04 |
| 16 | 53 | 9.0 | 450 | 0.14 | 240 | 241 | 241 | 240.7 | 0.15 | 91.78 | 0.68 | 0.01 |
| 17 | 53 | 9.0 | 450 | 0.14 | 240 | 240 | 240 | 240.0 | 0.17 | 92.15 | 0.66 | 0.00 |
| 18 | 53 | 9.0 | 450 | 0.14 | 240 | 241 | 241 | 240.7 | 0.27 | 91.39 | 0.77 | 0.00 |

| Sample Number | MeOH Mol % | MeSH Mol % TK711, TK751, TK773 53 ml catalyst | DMS Mol % | DMDS Mol % | MeOH Conversion % | MeSH Conversion % | MeSH Productivity % | Light Gas Conversion % | DMS Conversion % |
|---|---|---|---|---|---|---|---|---|---|
| | | | | feed | | | | | |
| 1 | 2.47 | 5.08 | 0.11 | 0.02 | 60.96 | 93.22 | 56.82 | 0.00 | 3.86 |
| 2 | 2.31 | 5.18 | 0.01 | 0.02 | 63.58 | 96.60 | 61.41 | 0.00 | 0.41 |
| 3 | 2.23 | 4.09 | 0.08 | 0.01 | 64.72 | 93.05 | 60.22 | 0.00 | 3.75 |
| 4 | 1.71 | 5.69 | 0.13 | 0.02 | 72.89 | 92.89 | 67.73 | 0.00 | 4.38 |
| 5 | 1.17 | 6.23 | 0.21 | 0.02 | 81.53 | 90.08 | 73.44 | 0.70 | 6.07 |
| 6 | 0.73 | 6.35 | 0.20 | 0.02 | 88.42 | 91.27 | 80.70 | 0.69 | 5.84 |
| 7 | 0.48 | 5.50 | 0.18 | 0.01 | 92.44 | 90.87 | 83.99 | 0.95 | 6.06 |
| 8 | 0.36 | 6.68 | 0.25 | 0.01 | 94.30 | 90.19 | 85.04 | 1.03 | 6.81 |
| 9 | 0.21 | 6.68 | 0.26 | 0.01 | 96.65 | 90.08 | 87.06 | 1.23 | 6.98 |
| 10 | 0.14 | 6.78 | 0.31 | 0.01 | 97.84 | 88.86 | 86.94 | 1.64 | 8.15 |
| 11 | 0.09 | 6.77 | 0.34 | 0.01 | 98.50 | 88.22 | 86.90 | 2.01 | 8.78 |
| 12 | 0.08 | 5.71 | 0.27 | 0.01 | 98.78 | 87.88 | 86.80 | 2.82 | 8.30 |
| 13 | 0.00 | 6.99 | 0.53 | 0.01 | 100.00 | 85.52 | 85.52 | 2.71 | 12.78 |
| 14 | 0.00 | 7.24 | 0.54 | 0.01 | 100.00 | 84.90 | 84.90 | 2.42 | 12.52 |
| 15 | 0.00 | 6.81 | 0.53 | 0.01 | 100.00 | 84.11 | 84.11 | 3.23 | 12.87 |
| 16 | 0.00 | 6.90 | 0.61 | 0.00 | 100.00 | 82.96 | 82.96 | 3.64 | 14.48 |
| 17 | 0.00 | 6.57 | 0.62 | 0.00 | 100.00 | 82.37 | 82.37 | 4.19 | 15.16 |
| 18 | 0.00 | 7.15 | 0.69 | 0.00 | 100.00 | 81.28 | 81.28 | 6.00 | 15.16 |

Based upon the results achieved with using the described catalyst blend loading, a weight average bed temperature (WAT) of 189° C.-241° C. was the optimal temperature range, which is substantially below the temperature of the "hot spot" often produced in prior art processes. As used herein, the term weight average bed temperature is the average of the temperatures measured across the reactor bed: $(T_1+T_2+\ldots+T_n)/n$. As an example, the weight average bed temperature for a reactor where the temperature is measured only at the reactor bed inlet and the reactor bed outlet is $(T_{outlet}+T_{inlet})/2$. A methanol liquid hourly space velocity (LHSV) of about 0.14 gr. liq./hr./gr. cat. to about 0.25 gr. liq./hr./gr. cat. was used.

While the invention has been shown or described in only some of its forms, it should be apparent to those skilled in the art that it is not so limited, but is susceptible to various changes without departing from the scope of the invention. For example, separate catalyst beds can be used for each different catalyst or a single catalyst bed can be used for the catalysts.

We claim:

1. A process for selective production of methyl mercaptan comprising the steps of:
   (a) contacting methanol and hydrogen sulfide with a graded catalyst bed, the graded catalyst bed comprising at least three catalysts having an activity for converting methanol to methyl mercaptan that increases from an inlet to an outlet of the graded bed and from a first catalyst to a second catalyst to a third catalyst; and
   (b) reacting the methanol and the hydrogen sulfide to produce a reactor effluent comprising the methyl mercaptan while maintaining near isothermal conditions during reaction of the methanol and the hydrogen sulfide.

2. The process of claim 1, wherein the graded catalyst bed comprises about 20% to about 35% of the first catalyst, about 20% to about 35% of the second catalyst, and about 35% to about 55% of the third catalyst.

3. The process of claim 1 having a hydrogen sulfide to methanol molar feed ratio in a range of about 6:1 to about 20:1.

4. The process of claim 1, wherein the first, second, and third catalysts comprise an oxide of molybdenum and an oxide of cobalt supported on alumina; an oxide of molybdenum and an oxide of nickel supported on alumina; or a combination thereof.

5. The process of claim 1, wherein the first, second, and third catalysts each have a stoichiometric sulfur uptake in a range of about 3 wt. % to about 13 wt. % and wherein the stoichiometric sulfur uptake increases from the first catalyst to the second catalyst to the third catalyst.

6. The process of claim 1 further comprising the step of supplying a sulfur source to the graded catalyst bed prior to the step of supplying the methanol and hydrogen sulfide to the graded catalyst bed.

7. The process of claim 1, wherein the first catalyst comprises about 0.5 wt. % to about 5 wt. % nickel monoxide, about 3 wt. % to about 10 wt. % molybdenum trioxide, and about 75 wt. % to about 95 wt. % alumina.

8. The process of claim 1, wherein the second catalyst comprises about 1 wt. % to about 3 wt. % nickel monoxide, about 5 wt. % to about 15 wt. % molybdenum trioxide, about 70 wt. % to about 90 wt. % alumina, and about 2 wt. % to about 8 wt. % aluminium phosphate.

9. The process of claim 1, wherein the third catalyst comprises about 1 wt. % to about 5 wt. % nickel monoxide, about 20 wt. % to about 30 wt. % molybdenum trioxide, about 50 wt. % to about 70 wt. % alumina, and about 5 wt. % to about 10 wt. % aluminium phosphate.

10. A process for selective production of methyl mercaptan comprising the steps of:
   (a) contacting methanol and hydrogen sulfide with a graded catalyst bed comprising at least three catalysts having an activity for converting methanol to the methyl mercaptan that increases from a first catalyst to a second catalyst to a third catalyst, the first catalyst being located upstream of the second catalyst and the second catalyst being located upstream of the third catalyst, the hydrogen sulfide and methanol being fed at a hydrogen sulfide to methanol molar feed ratio that ranges from about 6:1 to about 20:1; and
   (b) reacting the methanol and the hydrogen sulfide to produce a reactor effluent comprising the methyl mercaptan while maintaining near isothermal conditions during reaction of the methanol and the hydrogen sulfide, the reactor effluent comprising less than about 20 wt. % dimethyl sulfide.

11. The process of claim 10, wherein:
   (a) the first catalyst has a stoichiometric sulfur uptake in a range of about 3 wt. % to about 4 wt. %;
   (b) the second catalyst has a stoichiometric sulfur uptake in a range of about 4 wt % to about 5 wt. %; and
   (c) the third catalyst has a stoichiometric sulfur uptake in a range of about 11.5 wt. % to about 13 wt. %.

12. The process of claim 10, wherein the first catalyst has a bulk density greater than about 37 lbs/ft$^3$, the second catalyst has a bulk density greater than about 38 lbs/ft$^3$, and the third catalyst has a bulk density greater than about 51 lbs/ft$^3$.

13. The process of claim 10, wherein the first, second, and third catalysts comprise:
   (a) an oxide of molybdenum and an oxide of cobalt supported on alumina; or
   (b) an oxide of molybdenum and an oxide of nickel supported on alumina.

14. The process of claim 13, wherein the first, second, and third catalysts comprise about 0.5 wt. % to about 5 wt. % nickel monoxide, about 3 wt. % to about 30 wt. % molybdenum trioxide, and about 50 wt. % to about 95 wt. % alumina.

15. The process of claim 14, wherein the second and third catalysts further comprise about 2 wt. % to about 10 wt. % aluminium phosphate.

* * * * *